(12) United States Patent
Koenig et al.

(10) Patent No.: US 10,893,997 B2
(45) Date of Patent: Jan. 19, 2021

(54) REHABILITATION MECHANISM FOR PATIENTS CONFINED TO BED

(71) Applicant: REACTIVE ROBOTICS GMBH, Munich (DE)

(72) Inventors: Alexander Koenig, Munich (DE); Simon Spiegel, Munich (DE)

(73) Assignee: Reactive Robotics GmbH, Munich (DE)

( * ) Notice: Subject to any disclaimer, the term of this patent is extended or adjusted under 35 U.S.C. 154(b) by 369 days.

(21) Appl. No.: 15/767,723

(22) PCT Filed: Oct. 12, 2016

(86) PCT No.: PCT/DE2016/100475
§ 371 (c)(1),
(2) Date: Apr. 12, 2018

(87) PCT Pub. No.: WO2017/063639
PCT Pub. Date: Apr. 20, 2017

(65) Prior Publication Data
US 2018/0303696 A1    Oct. 25, 2018

(30) Foreign Application Priority Data

Oct. 13, 2015   (DE) .......................... 10 2015 117 435

(51) Int. Cl.
*A61H 1/02*     (2006.01)
*A61G 7/005*    (2006.01)
(Continued)

(52) U.S. Cl.
CPC ............. *A61H 1/0262* (2013.01); *A61H 1/02* (2013.01); *A61H 1/024* (2013.01); *A61H 1/0214* (2013.01);
(Continued)

(58) Field of Classification Search
CPC .......... A61H 1/00; A61H 1/02; A61H 1/0214; A61H 1/0218; A61H 1/0229;
(Continued)

(56) References Cited

U.S. PATENT DOCUMENTS 6,270,445 B1    8/2001   Dean, Jr. et al.
6,685,658 B1    2/2004   Dietz et al.
(Continued)

FOREIGN PATENT DOCUMENTS

DE          4113135 A1      10/1992
JP       H10258101 A        9/1998
(Continued)

*Primary Examiner* — Colin W Stuart
(74) *Attorney, Agent, or Firm* — Laurence A. Greenberg; Werner H. Stemer; Ralph E. Locher

(57) ABSTRACT

A rehabilitation mechanism rehabilitates the joints, muscles, and tendons of the legs of a bedridden patient in an automated manner according to a plan. A knee module can be operatively connected to the knee joint of the patient. A control module controls rehabilitation movements by way of the knee module. The knee module is a module to be arranged above the patient and the mattress, which module is supported directly or indirectly on a bed or the mattress frame, and includes a knee prosthesis which receives a knee joint of the patient, a connection element connected to the knee prosthesis, an extension arm to which the connection element is secured, and a mechanism to be actuated by the control module and which introduces a defined force into the knee prosthesis via the extension arm and the connection element to carry out rehabilitation movements according to a plan.

11 Claims, 9 Drawing Sheets

(51) Int. Cl.
*A61G 7/018* (2006.01)
*A61B 5/107* (2006.01)
*A61B 5/00* (2006.01)
*A61G 7/002* (2006.01)

(52) U.S. Cl.
CPC ......... *A61H 1/0218* (2013.01); *A61H 1/0229* (2013.01); *A61H 1/0237* (2013.01); *A61H 1/0244* (2013.01); *A61H 1/0255* (2013.01); *A61H 1/0266* (2013.01); *A61B 5/1071* (2013.01); *A61B 5/6891* (2013.01); *A61B 2505/09* (2013.01); *A61G 7/002* (2013.01); *A61G 7/005* (2013.01); *A61G 7/018* (2013.01); *A61H 2201/0138* (2013.01); *A61H 2201/0142* (2013.01); *A61H 2201/0146* (2013.01); *A61H 2201/1215* (2013.01); *A61H 2201/1418* (2013.01); *A61H 2201/1642* (2013.01); *A61H 2201/50* (2013.01); *A61H 2201/5007* (2013.01); *A61H 2201/5061* (2013.01); *A61H 2201/5069* (2013.01); *A61H 2205/10* (2013.01); *A61H 2205/102* (2013.01)

(58) Field of Classification Search
CPC .... A61H 1/0237; A61H 1/024; A61H 1/0244; A61H 1/0255; A61H 1/0259; A61H 1/0262; A61H 1/0266; A61H 2001/0211; A61H 2201/0138; A61H 2201/0142; A61H 2201/0146; A61H 2201/0149; A61H 2201/164; A61H 2201/1642; A61H 2201/5069; A61H 2201/5061; A61H 2203/0443; A61H 2203/0456; A61H 2205/10; A61H 2205/102; A61H 2230/62; A61H 2230/625; A61F 2/605; A61F 2/604; A61F 2/64; A61F 2002/607; A61F 2002/608; A61F 5/0123; A61F 5/0102; A61F 5/0127
See application file for complete search history.

(56) References Cited

U.S. PATENT DOCUMENTS

| | | | |
|---|---|---|---|
| 9,038,218 B1* | 5/2015 | Heil | A61G 5/006 5/618 |
| 2007/0043308 A1* | 2/2007 | Lee | A61H 1/0237 601/34 |
| 2010/0042022 A1 | 2/2010 | Kim et al. | |
| 2010/0113232 A1* | 5/2010 | Chen | A61H 1/0229 482/133 |
| 2010/0222716 A1* | 9/2010 | Olsen | A61H 1/00 601/26 |
| 2015/0320630 A1* | 11/2015 | Bucher | A61H 1/0262 601/26 |
| 2015/0342817 A1* | 12/2015 | Gu | A61H 1/0244 601/24 |
| 2015/0352394 A1* | 12/2015 | Marti | A63B 23/0494 482/139 |
| 2017/0035638 A1 | 2/2017 | Koenig | |

FOREIGN PATENT DOCUMENTS

| | | |
|---|---|---|
| JP | 2003225264 A | 8/2003 |
| JP | 2005334385 A | 12/2005 |
| WO | 0045897 A1 | 8/2000 |
| WO | 0061059 A1 | 10/2000 |
| WO | 2015158664 A1 | 10/2015 |

* cited by examiner

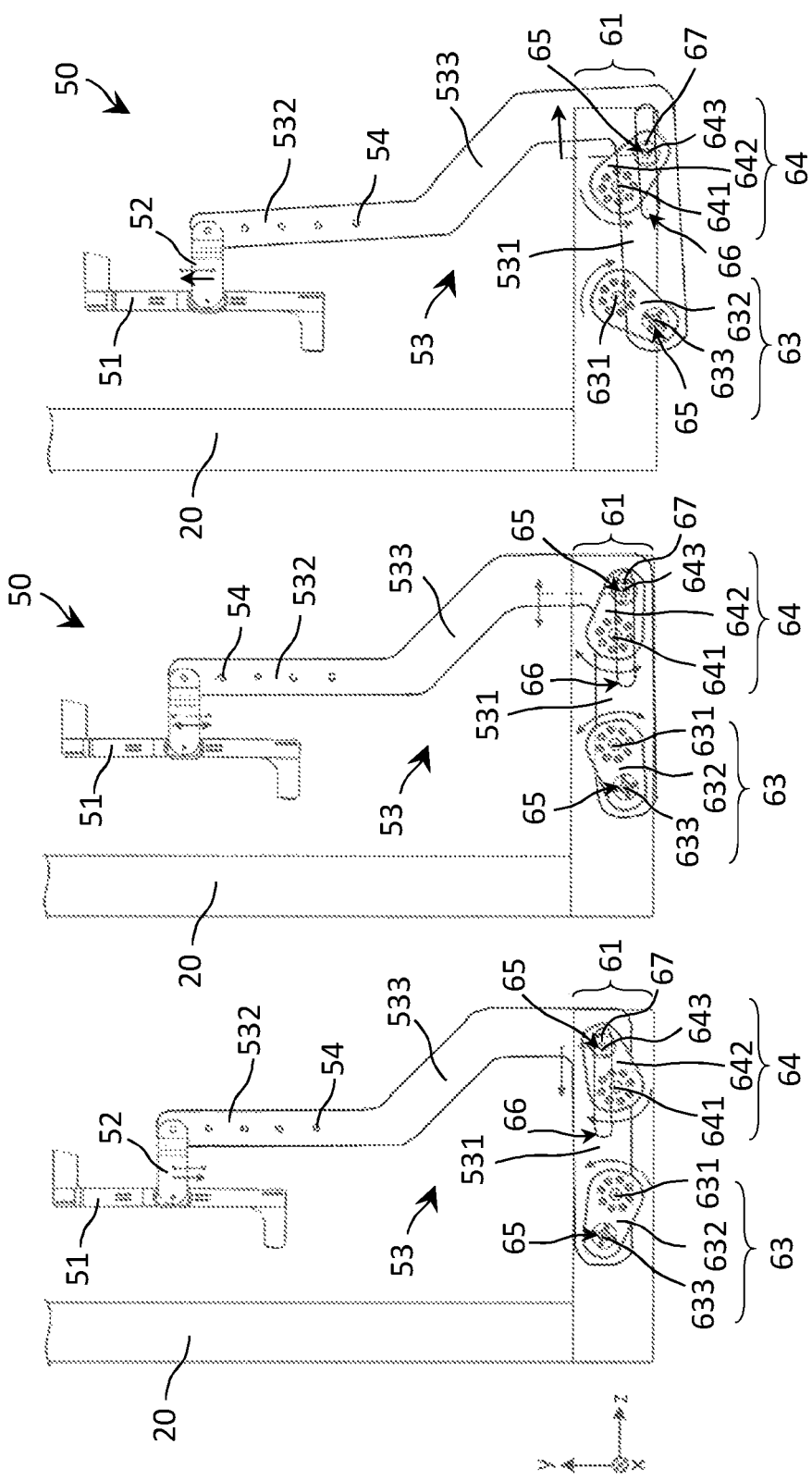

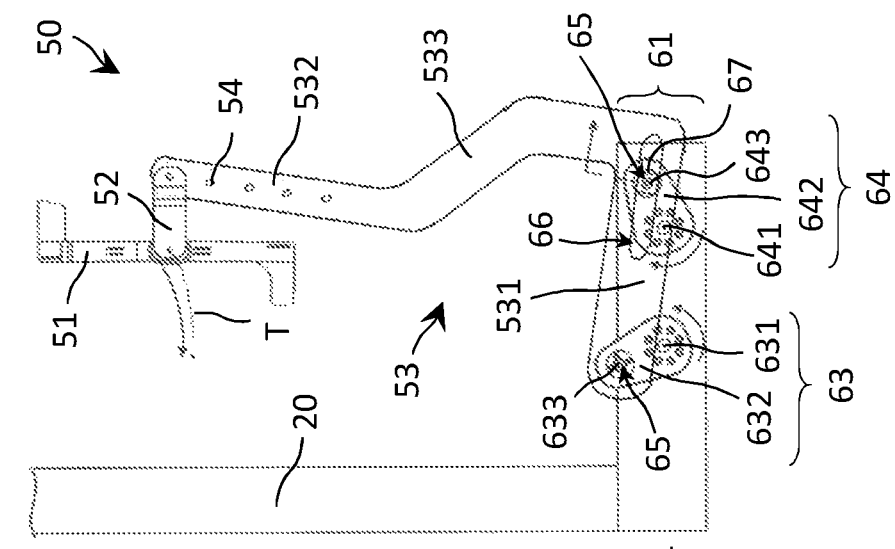
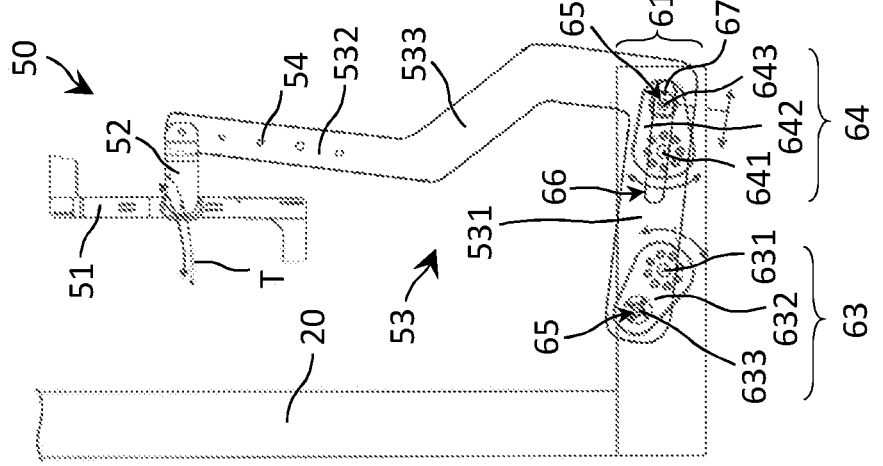
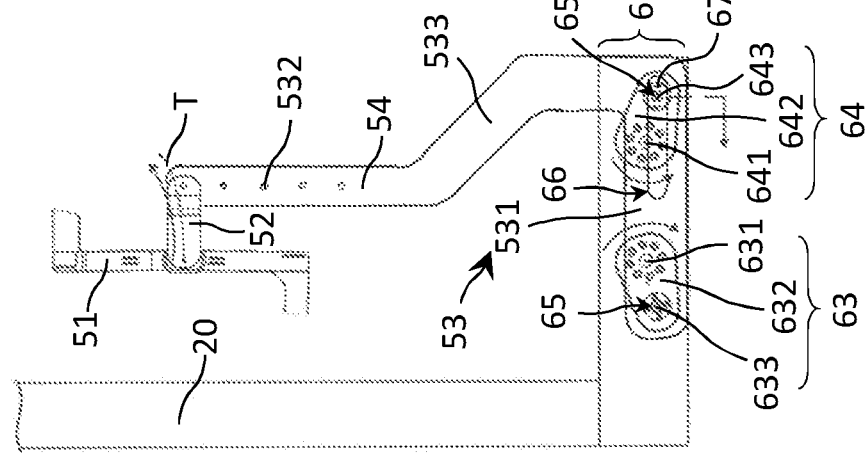

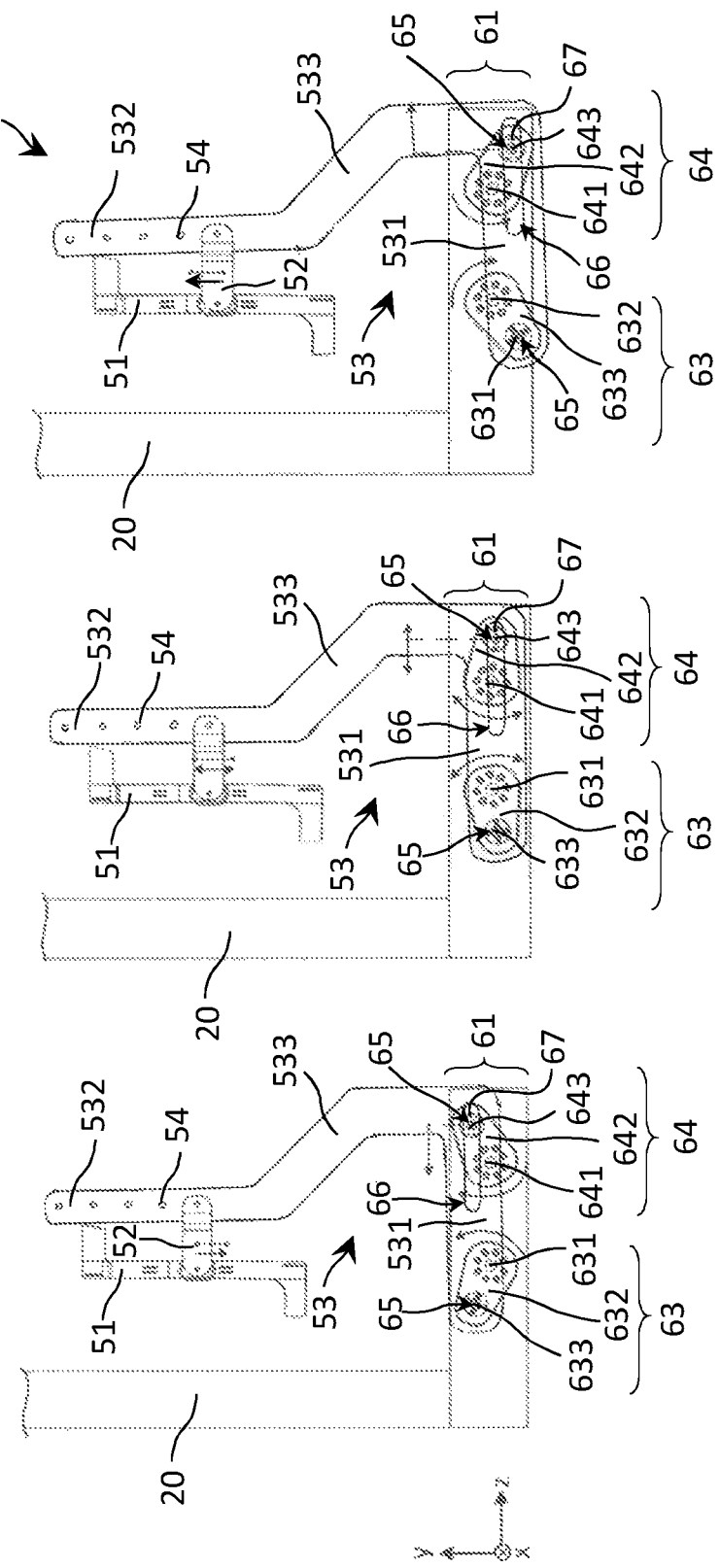

REHABILITATION MECHANISM FOR PATIENTS CONFINED TO BED

BACKGROUND OF THE INVENTION

Field of the Invention

The present invention relates to a rehabilitation mechanism for bedridden patients and to a method for actuating the rehabilitation mechanism, and also to a bed comprising the rehabilitation mechanism, in particular a care bed, a sickbed, a hospital bed or an intensive care bed.

Persons who are suffering from an illness or from the results of an accident, for example, or who are "bound" to a bed as a patient for other reasons and for longer than the normal nighttime rest periods (and who are referred to below as bedridden patients) often have restrictions on their activity which lead to such persons finding it difficult or even being unable to participate in social life following confinement to bed, that is to say being unable or only partially able to resume work and requiring assistance in daily life.

Through rehabilitation, the patient can regain some of his activity. In the medical field, rehabilitation is understood as the implementation and the effect of measures that are intended to reduce to a minimum the physical, psychological and social consequences of a handicap or limitation on activity (formerly disability, now activity) and an interruption of participation (formerly handicap; now participation) in social life.

Medical rehabilitation has proven to be particularly significant for the human locomotor system. If bones, joints, muscles and tendons, particularly of the human legs (comprising the buttocks, hip joint, thigh, knee joint, calf and foot) are not moved regularly, they become stiff, and the associated centers of locomotion situated in the human spinal cord may atrophy.

In contrast to persons who are physically able and have a stable circulatory state allowing them to participate in treadmill training for example, this training is typically denied to bedridden patients. Particular reasons may be orthopedic, intensive-care and/or neurological limitations on activity that are encountered individually or cumulatively.

Rehabilitation of Orthopedic Limitations on Activity

Orthopedics is the field of activity of a specialist in orthopedics and trauma surgery and deals with the occurrence, prevention, detection and treatment of congenital or acquired defects in the form or function of the musculoskeletal system, that is to say the bones, joints, muscles and tendons, and with the rehabilitation of such patients.

Orthopedic treatments include, among other things, surgical methods such as prosthetic surgery in particular (e.g., but not limited to, hip or knee joint replacement). After an accident or a surgical intervention, orthopedic limitations on activity mean that bedridden patients are typically unable to apply their full body weight to the bones, joints, muscles and tendons of one or both legs.

In order nevertheless to avoid stiffening of the legs, WO 00/45897 A1, for example, has disclosed an in-bed exercise machine which, when pushed up against the end of a care bed or sickbed, allows cyclical leg motions to be performed in a reclining position. However, the known in-bed exercise machine does not in particular allow exercises in a vertical position. In order for the feet to be fully or partially loaded by the patient's own weight, which can accelerate the healing process after a joint replacement or bone fracture for example, it is nevertheless necessary to be able to bring the bedridden patient completely or partially to a vertical position.

This aspect is taken into consideration, for example, by the standing table disclosed in WO 00/61059 A1. A problem is that said standing table and known devices comparable thereto are typically located in a separate training room, but in any case require the patient to be transferred from the bed to the respective rehabilitation device. At least for intensive care patients, i.e. for patients requiring intensive medical management, this is generally out of the question and is in any case associated with particular risks.

Rehabilitation of Intensive-Care Limitations on Activity

Intensive care is a medical specialty concerned with the diagnosis and therapy of life-threatening conditions and illnesses. Intensive care is typically provided in specially equipped units of a hospital or clinic, known as intensive care units, led by specially trained physicians such as anesthetists, internists, surgeons or neurologists.

The results of intensive care cover a wide range, depending on the underlying illness. In principle, there must be a positive prognosis of the illness. The goal of intensive care is namely to restore full health or at least to achieve a largely autonomous condition of the patient. So-called life-extending measures therefore are not pursued just for their own sake.

Intensive care units admit patients whose condition is life-threatening or could become life-threatening, particularly due to a weak cardiovascular system, a risk of cardiac arrest, risks of infection and the like. These circumstances are taken into account in standardized monitoring measures in intensive care units.

Intensive care units are elaborately equipped in terms of their structure and in terms of technical apparatus. A focal point lies in the design of the intensive care bed, which serves to safely support the most seriously ill patients in intensive care units. In addition to equipment that supports the monitoring measures, an intensive care bed is characterized particularly by a mattress which is suitably designed to prevent bedsores and to permit immediate manual resuscitation of at least the heart and/or lungs of an intensive care patient. The mattress also has to be non-conductive, for performing defibrillation, and resistant to liquids, blood and wipe-down disinfections using commercially available disinfecting agents. In order to secure intensive care patients against falling out of bed, the mattress is usually enclosed by barriers on the longitudinal and transverse sides, which barriers can be attached to the longitudinal and transverse sides of a bed or mattress frame and often support at least part of the monitoring apparatus.

On account of this typical design of intensive care beds, the known rehabilitation devices described above cannot be easily brought adjacent to a modern intensive care bed and/or require repositioning of the patient. However, as has already been mentioned, this repositioning is generally out of the question for intensive care patients, who are normally weak or require intensive care for other reasons, and it is in any case associated with particular risks.

Meanwhile, patients in intensive care facilities already have a five to ten times higher risk of infection compared to patients in normal units. Various infection-promoting factors add up in intensive care patients, which factors may originate both from the patients themselves and also from the treatment measures used in intensive care (many catheters, tubes, etc.). Therefore, in order to reduce the risk of infection, special hygiene measures are specified for intensive care units, and rehabilitation devices such as the known in-bed exercise machine or the known standing table satisfy such specifications only with difficulty.

Therefore, rehabilitation strategies supported by rehabilitation devices have hitherto typically been used only after the patient has left the intensive care unit.

Rehabilitation of Neurological Limitations on Activity

Neurology is the study of diseases of the nervous system. The organ systems that are taken into consideration in neurology are the central nervous system, i.e. the brain and spinal cord, the surrounding structures and blood supply vessels thereof, and the peripheral nervous system including the structures thereof connecting to the muscles and the musculature.

Recent studies in neurological rehabilitation have shown that rehabilitation should begin as early as possible. For example, in order to maximize the success of rehabilitation, rehabilitation measures should be started just 24 hours after a stroke exhibiting paraplegia or other paralysis or after a traumatic brain injury with or without quantitative loss of consciousness, presenting as a coma in its most severe form.

Since patients affected by paralysis and/or loss of consciousness are typically still in an intensive care unit at this point in time, neurological rehabilitation strategies that are to be begun at an early stage are doubly difficult: in addition to the problematic intensive care environment described above, the entire leg motion, at least in the case of paralyzed and/or comatose patients, must be performed cyclically at least at the outset solely by the rehabilitation device.

In this connection, it is particularly problematic that the position of the patient in the bed is generally undefined. In order to produce the contact between patient and rehabilitation device, the patient can be moved until suitable sections in particular of his leg coincide with suitable contact points of a rehabilitation device, or an attempt can be made to adjust the position of the rehabilitation device to the patient until sufficient coincidence is achieved. Both of the described scenarios require time and are also susceptible to error, since the coincidence usually has to be obtained manually and is thus not perfect.

The following problem is also encountered: When therapy by means of a rehabilitation device begins, it can generally happen that the patient slips, for example when the bed is brought completely or partially to a vertical position and the force of gravity draws the patient downward. Previously adjusted contact points between the rehabilitation device and suitable limbs, in particular the legs of a patient, would no longer lie optimally in relation to one another. To readjust the contact points, the rehabilitation device has to be stopped and oriented again before a therapy can be continued.

For these reasons, exercises aimed at keeping patients in intensive care facilities active are mostly performed by specialized physiotherapists who manually move the limbs of intensive care patients, daily if possible, but at least several times a week. This manual physiotherapy has the disadvantage that the therapists can quickly become tired due to the physical exertion, leading to difficulty in planning, let alone evaluating, the progress made in a session. Furthermore, it is not guaranteed that the physiotherapist will work at the same (maximum) effort and efficiency at each physiotherapy session. Moreover, the physiotherapist cannot perform an objective assessment of the activity of the patient, only a subjective one, which makes objective assessment of the success of the therapy over several therapy sessions difficult. Finally, in particular in the intensive care environment, a therapy session may require not only the presence of one or more physiotherapists, but also the presence of the nurse who has to monitor the vital parameters of the patient during the session, for example in order to be able to react to cardiovascular problems. The additional presence of highly qualified clinical personnel means that such therapy sessions are difficult to afford.

BRIEF SUMMARY OF THE INVENTION

Proceeding from this, the object of the present invention is to make available an improved rehabilitation mechanism in comparison with the prior art, particularly for patients who are bedridden due to orthopedic, intensive care and/or neurological limitations on activity, which rehabilitation mechanism permits planned, automated rehabilitation of at least the joints, muscles and tendons of the legs of bedridden patients, without the patients having to be transferred between beds. Moreover, a preferably configured rehabilitation mechanism according to the invention should be able to be adjusted, wholly or partially automatically, to altered contact points between the rehabilitation mechanism and suitable limbs, in particular the legs of a patient. In addition to commercially available or specially made care beds or sickbeds, the rehabilitation mechanism should finally also be usable in commercially available or specially made hospital beds or intensive care beds, regardless of whether the bedridden patient in the respective bed can be brought wholly or partially to a vertical position, wherein the rehabilitation mechanism is intended to be able to support a rhythmic loading and unloading of the soles of the feet of bedridden patients in any position of the bedridden patient between a horizontal position and a vertical position.

This object is achieved in the first instance by a rehabilitation mechanism having the features as claimed.

A rehabilitation mechanism according to the invention, which is designed to be suitable for a planned, automated rehabilitation of at least the joints, muscles and tendons of the legs of a bedridden patient, comprises at least:
  a knee module which can be operatively connected to the knee joints of the bedridden patient, and
  a control module for controlling planned rehabilitation movements at least of the joints, muscles and tendons of the legs of the bedridden patient by means of the knee module.

It is additionally characterized in that the knee module is designed as a module which can be arranged above the patient and the mattress and which is supported directly or indirectly on a bed frame or mattress frame and comprises at least:
  a knee orthosis which receives a knee joint of the bedridden patient;
  a connection element which is connected to the knee orthosis, preferably in an articulated manner;
  an extension arm to which the connection element is secured, preferably rigidly or at least in a way that can be made rigid, and
  a mechanical device which can be actuated by means of the control module and which, by way of the extension arm and the connection element, introduces a defined force (N) into the knee orthosis such that the joints, muscles and tendons of this leg perform planned rehabilitation movements via the bedridden patient's knee joint which is received in the knee orthosis.

The modular design of the rehabilitation mechanism has the advantage that bedridden patients, in particular intensive care patients, can receive planned, automated rehabilitation directly in their bed, specifically without the risk involved in transfer between beds and/or without having to contribute cooperatively.

The terms "module" and "modular design" are to be understood below as meaning in particular that the components thus designated form individual, self-contained assemblies, which specifically are operatively connected to further elements but are reversibly separable from the latter for the purpose of storage and/or transport.

By arranging a knee module above the patient and the mattress and supporting it directly or indirectly on a bed frame or mattress frame, it is possible in particular to apply to the knee joint of bedridden patients a supporting force that advantageously rhythmically loads and unloads the soles of the feet of said patients, specifically in any position adopted by the patient between a horizontal and a vertical position.

In the case of orthopedic patients, the rhythmic loading and unloading of the soles of the feet is important, for example in order to accustom an injured joint to walking again and/or to a load in a partially or fully vertical position.

In the case of intensive care patients, the rhythmic loading and unloading of the soles of the feet is significant in order to prevent stiffening of the legs and atrophy of the centers of locomotion situated in the spinal cord.

In the case of neurological patients, the alternating motion generates additional sensory input in the soles of the feet, said input being transmitted to the central nervous system. This "efferent sensory input" ensures that the brain regions involved in the generation of walking movements are also excited.

In light of the above, it is therefore preferable, in one development, that a rehabilitation mechanism further comprises a foot module which can be operatively connected to the feet and/or in particular the soles of the bedridden patient.

The modules, in particular the knee module or also an optional foot module, can be completely separated and removed mechanically and electrically from a bed on which they are used and can thus be stowed away separately. Alternatively or in addition, these modules can be folded away, for example in a space underneath a mattress of a bed.

The modularity/removability/separability of the knee module and of an optional foot module from the bed, whether by separating or by storing the therapy modules beneath the bed, is particularly advantageous since the bed can be used as a normal bed outside of the therapy periods. The term "normal use" is to be understood here as meaning that no element of the rehabilitation mechanism prevents access to the patient from all sides in any form, prevents transfer from or into the bed, or prevents or hinders any necessary emergency measures or care measures.

Regarding the therapeutic context of the present invention, mention is also made here of WO 2015/158664 A1 filed by the applicant, the full content of which document is referred to here by way of precaution, in particular also as regards the foot module variants described therein.

The present invention therefore also relates to a bed comprising the rehabilitation mechanism according to the invention, it being possible for said bed to be designed, for example, as a commercially available or specially built care bed, sickbed, hospital bed or in particular as an intensive care bed.

The rehabilitation mechanism is preferably able to be fastened in a reversible and releasable manner to a sickbed, in particular a conventional sickbed. For this purpose, it is provided and designed to be arranged reversibly on conventional sickbeds in order that a patient lying in the bed can undergo therapy. The rehabilitation mechanism preferably has supporting and/or clamping means in order to achieve the reversible fastening. The rehabilitation mechanism is preferably designed to be detachable as a module from a sickbed, in particular a conventional sickbed, and/or to be stowed underneath the sickbed. This greatly simplifies the use of the rehabilitation mechanism. It represents a self-contained system which can be used selectively on existing sickbeds.

The planned automated rehabilitation, using a rehabilitation mechanism according to the invention, at least of the joints, muscles and tendons of the legs of bedridden patients, in particular intensive care patients, has the aim of minimizing the limitations on activity and/or the interruption of participation in social life. The central therapeutic idea behind this is to quantify and/or control to a desired level the activity of bedridden patients, in particular intensive care patients, as early as possible, that is to say while they are still confined to bed. The determination of the individual parameters of a planned automated rehabilitation in this respect, in the context of the present invention, is nevertheless the responsibility of physiotherapists or of at least comparably trained staff.

The rehabilitation movement is particularly preferably a walking movement, a stepping movement and/or a movement simulating the climbing of stairs. A walking movement, a stepping movement or a movement simulating the climbing of stairs is substantially more advantageous for rehabilitation than a cycling movement, for example. DE 41 13 135 A1, for example, discloses a pure foot module which allows a cycling movement. However, it is far more important for rehabilitation patients to acquire a walking movement, a stepping movement or a movement simulating the climbing of stairs and to simulate the loads occurring during such a walking movement, a stepping movement or a movement simulating the climbing of stairs, and to measure progress thereby. A cycling movement is suitable only under certain conditions, since here in particular there is no rolling of the foot, and a torque applied to the ankle joint of the foot tends to be low.

According to a preferred development of the invention, the foot module and the knee module together form an exoskeleton for the patient. The modules forming the exoskeleton interact by means of the control module and assist the patient in performing the movement.

Moreover, the rehabilitation mechanism preferably comprises a biofeedback module for providing visual and/or audible feedback to the patient. Such a biofeedback module preferably has a display or the like which is arranged in the field of vision of the patient in order to give feedback to the latter. Such a biofeedback module can be designed in principle as disclosed in US 2010/0042022 A1. It is preferably designed to indicate to the patient when said patient is performing a movement correctly and/or is making progress. Moreover, the biofeedback module is preferably designed to indicate to the patient when said patient is not performing a movement correctly, should change exercises, should stop an exercise, and so on.

Further advantageous embodiments and developments which can be used individually or in combination with one another are the subject matter of the dependent claims.

These and additional details and further advantages of the invention are described below on the basis of preferred illustrative embodiments, to which the present invention is not however limited, and in conjunction with the accompanying schematic drawing.

BRIEF DESCRIPTION OF THE SEVERAL
VIEWS OF THE DRAWING

FIG. 1 a perspective view of a bedridden patient or intensive care patient in a commercially available bed according to the prior art, in particular an intensive care bed, with longitudinal barriers and transverse barriers, in particular a barrier plate arranged at the head or feet end;

FIG. 2 the bed from FIG. 1 with a rehabilitation mechanism arranged at the feet end in place of a commercially available barrier plate or, as shown, by means of a specially statically configured support plate;

FIG. 3 a perspective view of a detail of the rehabilitation mechanism shown in FIG. 3;

FIG. 4 a perspective side view of the bed from FIG. 3, with a patient secured to the bed and with a fitted knee module and foot module of a rehabilitation mechanism before the bed is placed vertically;

FIG. 5 the bed from FIG. 3 in a vertical state;

FIG. 6 an enlarged perspective view of the rehabilitation mechanism according to the invention from FIG. 5;

FIG. 7 a front view of the rehabilitation mechanism from FIG. 6;

FIGS. 8a to 8c and FIGS. 10a to 10c show an automated adjustment after alteration of the contact points between the rehabilitation mechanism and the limbs of a patient with long legs (FIGS. 8a to 8c) or with short legs (FIGS. 10a to 10c);

FIGS. 9a to 9c and FIGS. 11a to 11c show the trajectories (T) generated by the rehabilitation mechanism via the knee orthosis for bending or extending the legs of a patient with long legs (FIGS. 9a to 9c) or with short legs (FIGS. 11a to 11c);

Figure 12:
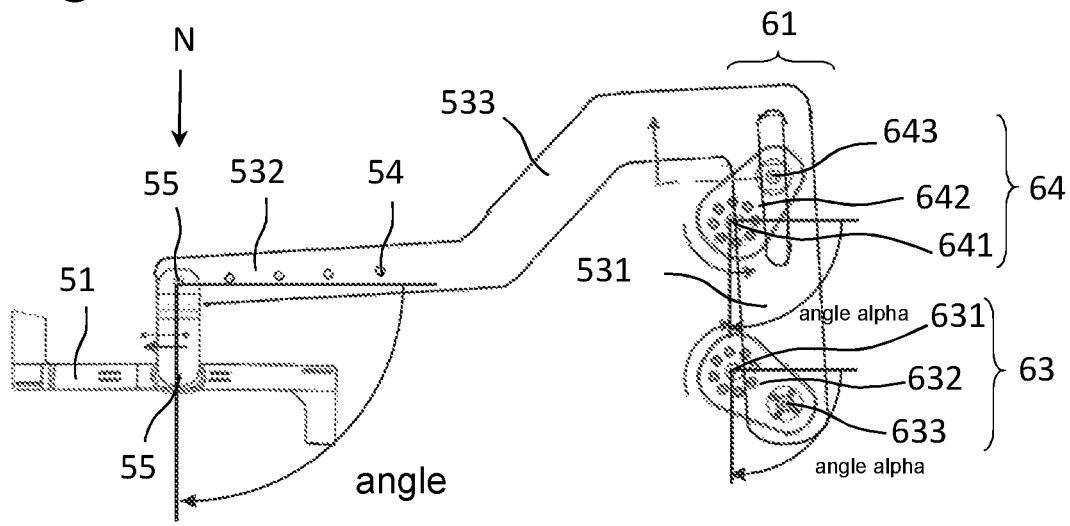
Figure 13:
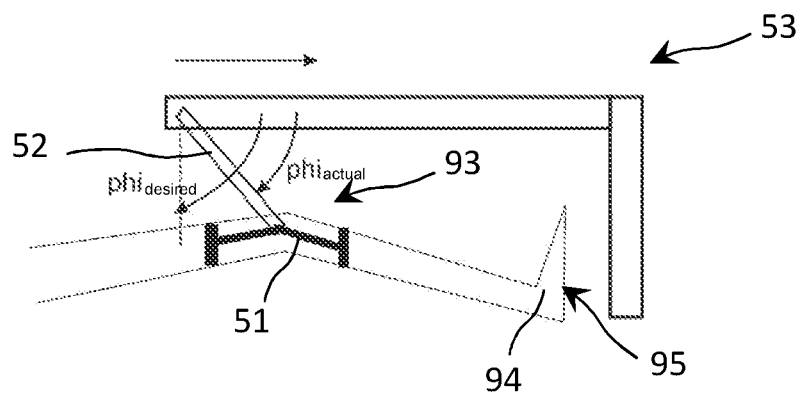
Figure 14:
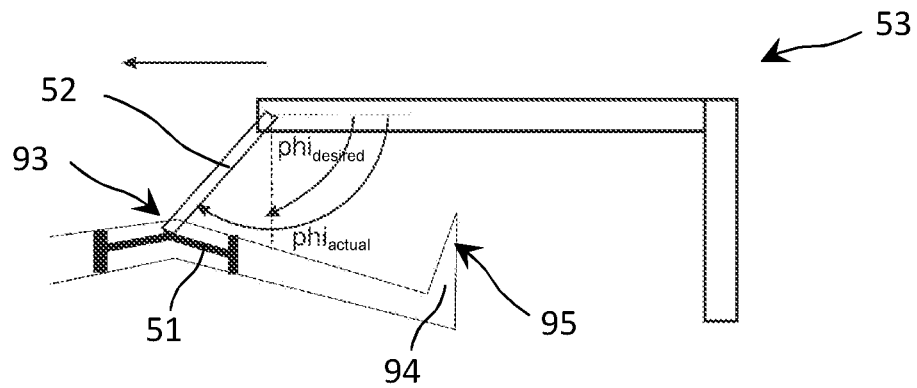
Figure 15:
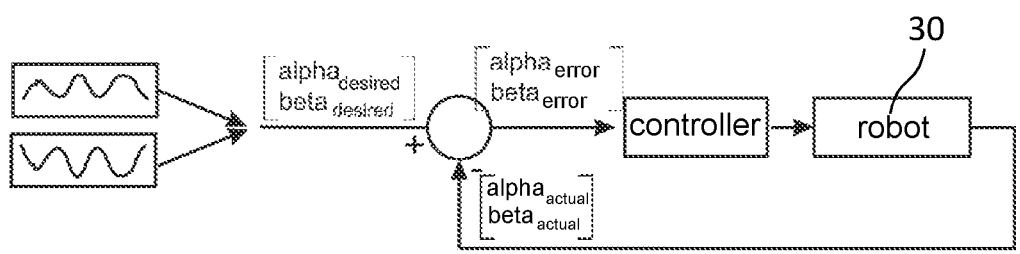
Figure 16:
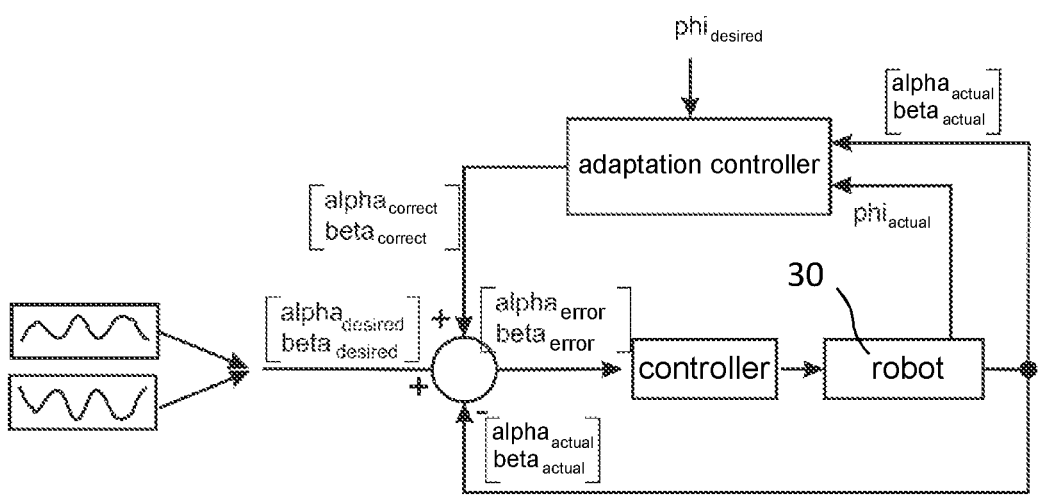

FIG. 12 an enlarged view of the extension arm from FIG. 8c for example, how the angle phi ($\varphi$) adopted by the connection element to the knee orthosis and/or to the extension arm can be monitored by means of at least one angle sensor;

FIG. 13 how, deviating from a desired angle setting ($\varphi\_desired$), the knee joint of a patient can be shifted in the direction of the foot end of the bed;

FIG. 14 how, deviating from a desired angle setting ($\varphi\_desired$), the knee joint of a patient can be shifted in the direction of the head end of the bed;

FIG. 15 a schematic diagram of a control circuit for generating a planned rehabilitation movement by means of a rehabilitation mechanism; and FIG. 16 a schematic diagram of a control circuit, expanded in relation to FIG. 15, for generating an adjustment of the eccentrics of a rehabilitation mechanism, which adjustment is effected either sequentially or simultaneously with respect to planned rehabilitation movements.

In the following description of preferred embodiments of the present invention, identical reference signs designate identical or comparable components.

DESCRIPTION OF THE INVENTION

Figure 1:
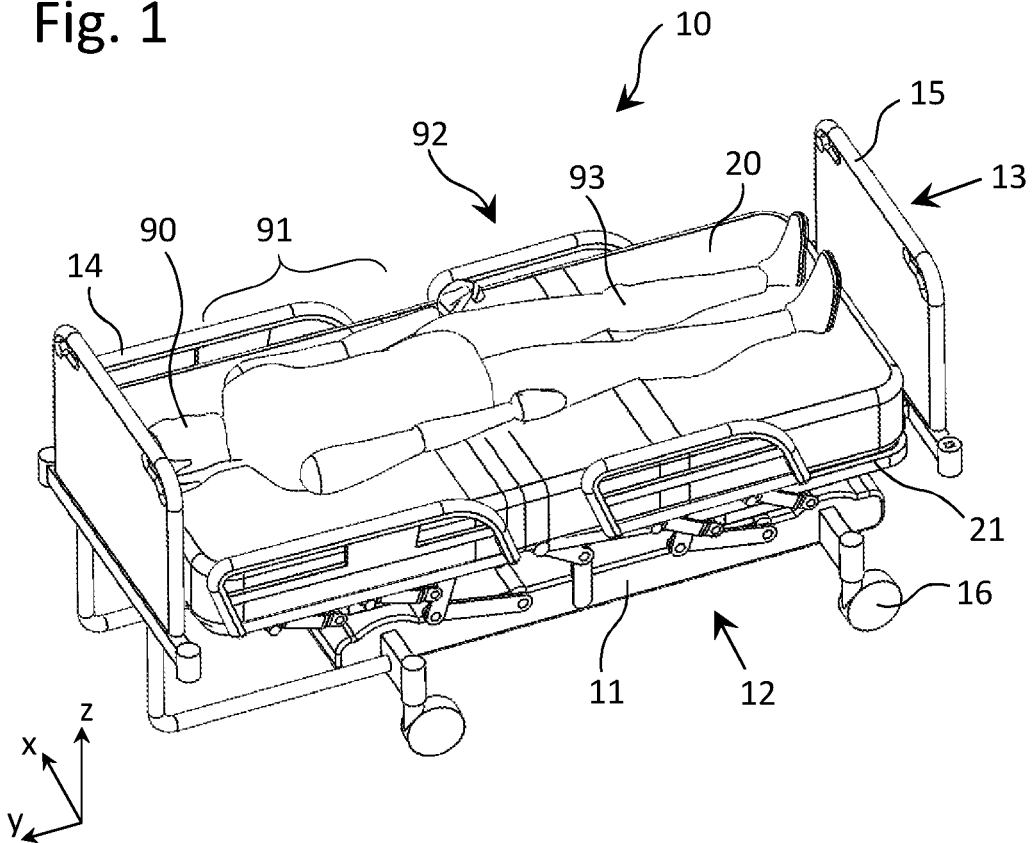

FIG. 1 shows a perspective view of a patient 90, who is bedridden or requires intensive care, in a commercially available bed 10 according to the prior art, in particular an intensive care bed. The bed 10 shown can be designed in particular for the medical demands that are typically placed on intensive care beds, but it can also be used in a non-intensive care environment, in particular as a care bed, sickbed or hospital bed. In addition to equipment (not shown) supporting the monitoring measures, the bed 10 shown in characterized by a mattress 20 suitably designed at least to prevent bedsores. In the case of an intensive care bed, the bed 10 shown is further characterized by a mattress 20 which is additionally designed to permit immediate manual resuscitation of at least the heart and/or lungs 91 of an intensive care patient 90, is non-conductive in order to allow defibrillation to be carried out, and is resistant to liquids, blood and wipe-down disinfections with commercially available disinfecting agents, wherein undivided or continuously configured mattresses 20 are preferable for reasons relating to cleaning and disinfection. In order to secure bedridden patients 90, in particular intensive care patients, against falling out of bed, the mattress 20 is enclosed completely or partially by longitudinal barriers 14 and transverse barriers 15 which, for example, can be fastened to longitudinal sides 12 and transverse sides 13 of a bed frame 11 or mattress frame 21 of the bed 10, which sides typically support at least some of the monitoring equipment (not shown). To be able to move the bed 10, it has castors 16, for example. To improve maneuverability, the castors 16 can be designed to be driven by motor. Embodiments are also preferred in which the bed frame 11 and/or mattress frame 21 are designed to be adjustable in height and/or in inclination (whether lengthwise or crosswise), wherein the head end and the foot end can preferably be designed to be adjustable separately, i.e. with different and/or mutually opposite inclinations (not shown).

Figure 2:
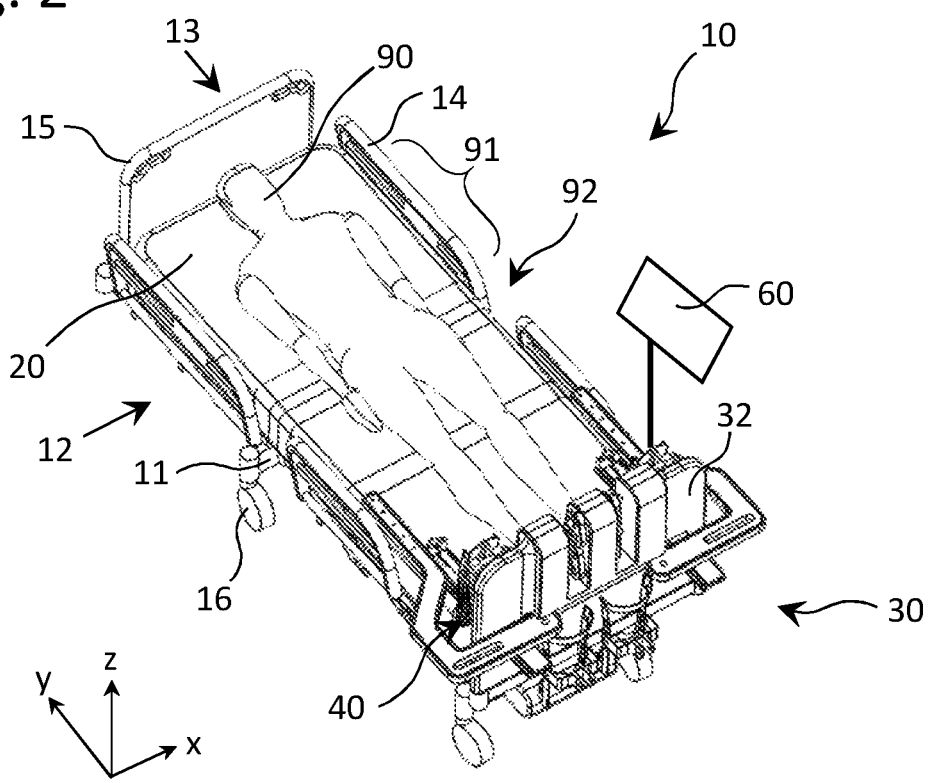

FIG. 2 shows the bed 10 from FIG. 1 with a rehabilitation mechanism 30 arranged at the foot end in place of a commercially available barrier plate or, as shown, by means of a specially statically configured support plate 32. It can be seen how the rehabilitation mechanism 30 can be brought into a storage position on the bed 10 such that it advantageously causes no lasting inconvenience to the patient 90.

Figure 3:
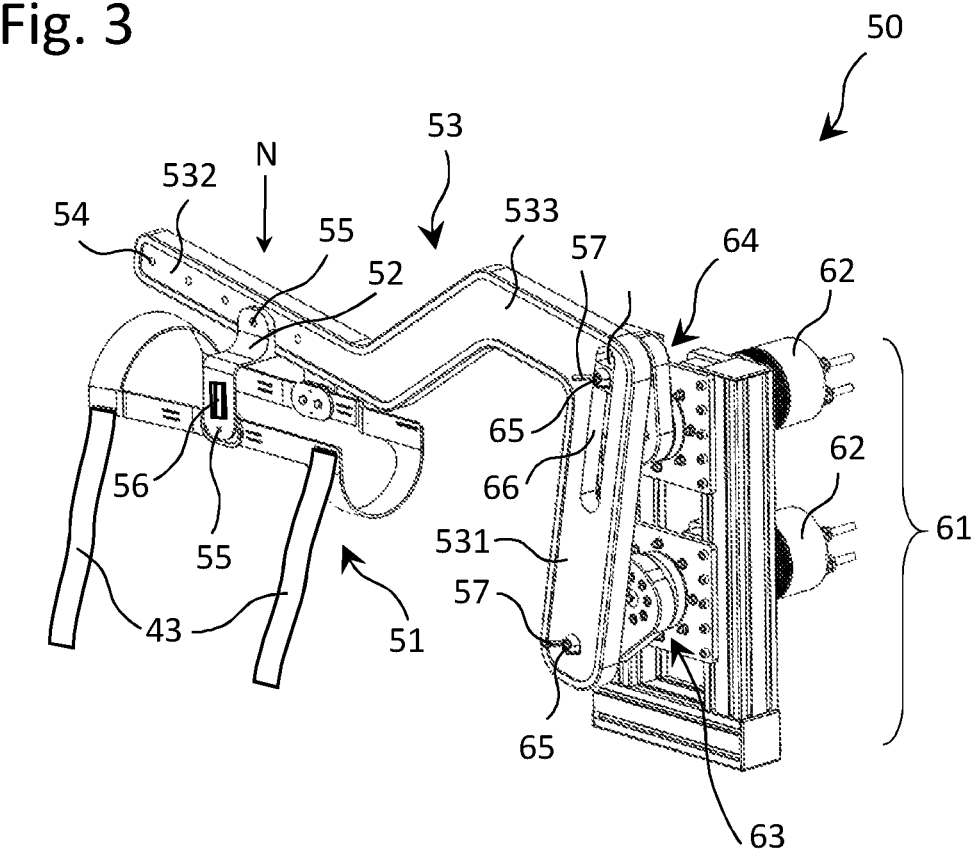

FIG. 3 shows a perspective view of a detail of the left extension arm 53 of the knee module 50 of the rehabilitation mechanism 30 shown in FIG. 2. It can be seen how the distal end or portion 531 and the proximal end or portion 532 of the extension arm 53 are connected to each other via a middle portion 533, which is preferably designed bridging them in such a way that sufficient clearance is ensured for the foot 94 of the patient 90. In addition, the proximal portion 532 of the extension arm 53 carrying a knee orthosis 51 via the connection element 52 can be connected to two motor-driven eccentrics 63 and 64 by means of axial securing elements, for example clamps, levers, click connectors (not shown) or, as shown, by means of two butterfly nuts 57 that can be screwed for example onto the control pins 633 and 643 (see FIGS. 8 to 11 in this regard).

Before the therapy is started or the bed 10 is moved to a vertical position, the therapist brings the distal end of the knee module 50, i.e. the distal end 531 of an extension arm 53, via the releasable pin connection (for example butterfly nut 57 in conjunction with control pin 633 or 643) to the support plate 32 and in particular to the eccentrics 63, 64 used for the drive (motor 45) of the extension arm 53. At the proximal end 532 of the extension arm 53 of the knee module 50, the knee orthosis 51 is placed on the knee 93 of the patient 90 and secured by the therapist to the lower leg and upper leg of the patient 90 via fixing straps 43.

If a foot module 40 is preferred in addition to the knee module 50, the foot module 40 can be shifted preferably via a linear mechanism 41 in the y direction, for adaptation to the height of the patient 90, and in the x direction, for adaptation to the width of the legs 90, and thereafter can be fixed to the support plate 32, for example via a clamping mechanism (not shown). The foot of the patient 90 is secured to the tread surface 42 of the foot module [40] via fixing straps 43 (FIG. 6).

The support plate 32 thus has a linear mechanism 41 in order to be able to move a foot module 40 inside the support plate 32. Moreover, at least the electric motors 62, for driving the two eccentrics 63, 64 per extension arm 53, the control module 60 and the eccentrics 63, 64 themselves are preferably integrated in the support plate 32. To transmit the loads to the bed 10, the connection between support plate 32 and bed 10 must have a high degree of stiffness. For the use of the rehabilitation mechanism 30 in commercially available beds 10, a statically modified support plate 32 is thus preferred.

Figure 4:
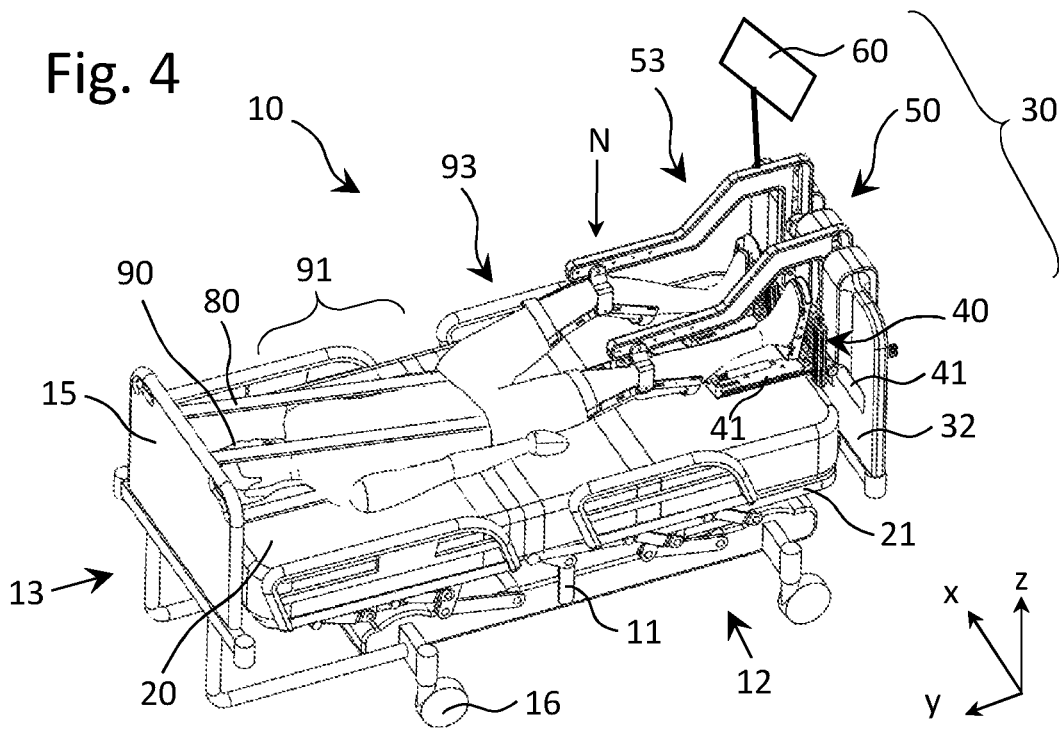

FIG. 4 shows a perspective view of the bed 10 from FIG. 3 with a patient 90 (secured to the bed 10) and with the fitted knee module 50 and foot module 40 of a rehabilitation mechanism 30 prior to the bed 10 being moved to a vertical position.

Figure 5:
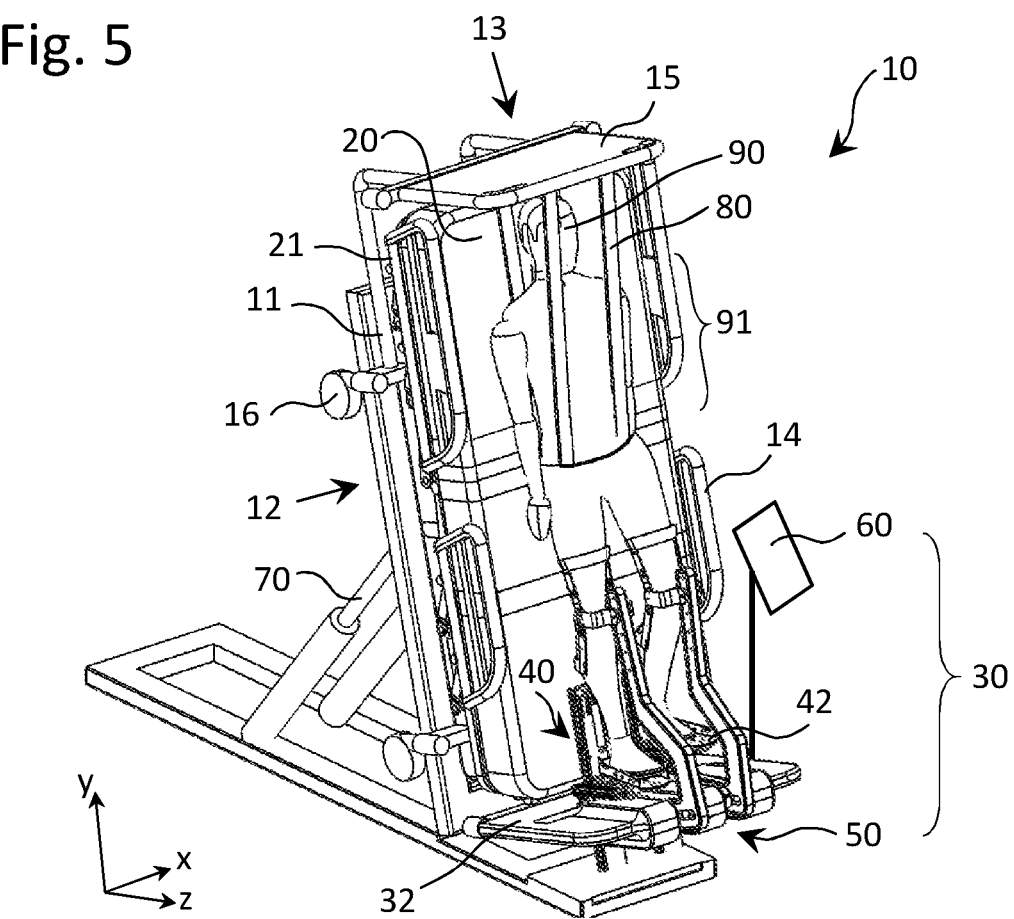
Figure 6:
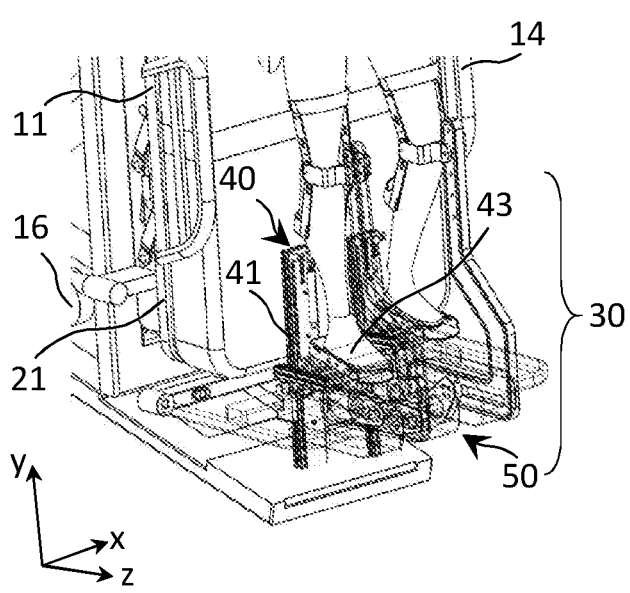
Figure 7:
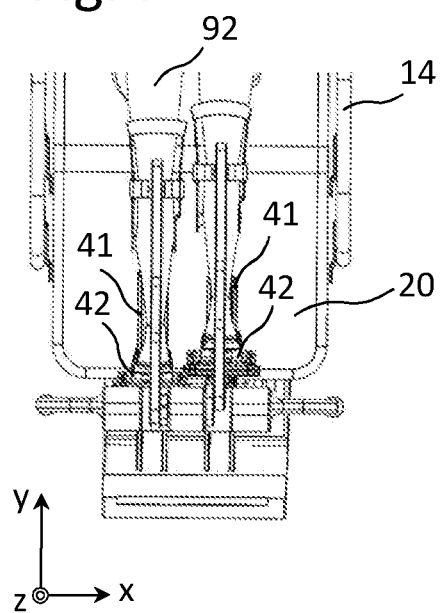

FIG. 5 shows the bed 10 from FIG. 4 in a vertical state, FIG. 6 shows the rehabilitation mechanism 30 from FIG. 5 in an enlarged perspective view, and FIG. 7 shows a front view of the rehabilitation mechanism 30 from FIG. 6 for generating a stepping movement, etc.

The rehabilitation mechanism 30, consisting according to the invention of control module 60 and the knee module 50 with knee orthosis 51, connection element 52 and extension arm 53, and preferably among other things with the foot module 40 as tread surface 42 and fixing straps 43, and with the bed 10, is brought by the adjustment mechanism 70 to a vertical position for the application and the duration of the therapy. The patient 90 is supported in the bed not only by foot module 40 and knee module 50 but also by a stabilizing mechanism 80.

The rehabilitation mechanism 30 for generating planned rehabilitation movements, in particular a stepping movement of the legs 92 of the patient 90 and/or a movement simulating the climbing of stairs, and for automated adjustment after an alteration of the contact points between the knee orthosis 51 receiving the limbs of the patient (knee joint 93 should always lie at the height of a central hinge of the orthosis 51) and the rehabilitation mechanism 30, is described below.

The extension arms 53, which induce a movement of the legs 92 of the patient 90 via the connection element 52 and the knee orthosis 51, are each driven by a rotation of two eccentrics 63, 64. The rotation of the eccentrics 63, 64 is in turn generated by an electric motor 62 via the drive of the shaft 631 of the first eccentric 631 and the shaft 641 of the second eccentric 641. The movement is transmitted to the respective extension arm 53 via the control pins 633, 643 of the first and second eccentrics 632, 642. The respective extension arm 53 is mounted onto the control pins 632, 642 and secured against axial displacement. On account of a rotary sliding bearing 65, the control pin 633 of the first eccentric 632 has a rotational degree of freedom relative to the extension arm 53. On account of a linear guide 66, here indicated as a slide block 67 (see FIG. 3), and of a rotary sliding bearing inside the linear guide 66, the control pin 643 of the second eccentric 642 has a degree of freedom relative to the extension arm 53 both in translation and also in rotation.

In order to adapt the rehabilitation mechanism 30 to the different anthropometries of the patients 90 and to different distances of the patient 90 from the support plate 32, the connection element 52 can be mounted in different receiving points 54 or by means of a linear carriage (not shown) on the extension arm 53. The connection element 52 (at least at one end, for the adjustment if appropriate initially at both ends) is mounted (and later secured at least at one end) in an articulated manner on the knee orthosis 51. The connection of the connection element 52 to the extension arm 53 has a rotary degree of freedom up to and including the adjustment of the final position of the patient 90. At the start of therapy, this degree of freedom is preferably removed, e.g. by manual locking, such that the connection between connection element 52 and extension arm 53 is rigid during therapy.

FIGS. 8a to 8c and FIGS. 10a to 10c show an automated adjustment after alteration of the contact points between the rehabilitation mechanism 30 and the limbs of a patient 90 with long legs 92 (FIGS. 8a to 8c) or with short legs 92 (FIGS. 10a to 10C).

As can be seen from FIGS. 8a to 8c, the connection element 52 in receiving point 54 on the extension arm 53 has a greater distance to the distal end or portion 531 of the extension arm 53 than in a patient 90 with a short leg length. This case is shown in FIGS. 10a to 10c, from which it can be seen that the connection element 52 in receiving point 54 on the extension arm 53 has a shortest distance to the distal end or portion 531 of the extension arm 53.

FIGS. 8a and 10a show the initial state after manual fastening of knee orthosis 51 and connection element 52 to the extension arm 53. When the bed 10 is moved to a vertical position, the patient 90 slips, as do his joints, generally in the negative y direction. Through the combination of a defined rotational movement on the control pin 632 of the first eccentric 63 (rotation of the shaft 631 of the first eccentric 63 about the x axis) and a defined rotational and translational movement on the control pin 642 of the second eccentric 64 (rotation of the shaft 641 of the second eccentric 641 about the x axis, translational movement of the slide block 67 along the extension arm 53), it is possible to obtain a translational movement of the connection element 52 along the y axis likewise in a negative direction, such that the displacement of the hinge points, here in the negative y direction, caused by the slipping of the patient 90 can be compensated. Generally, as is shown in FIG. 8b and FIG. 10b, movements of the connection element 52 can be effected in positive and negative y direction by the mechanism. FIGS. 8c and 10c show the orientation of the eccentrics 63, 64 after automated adjustment to slipping of the patient 90 in the negative y direction.

The aim of the automated adjustment is the introduction of force N at a defined angle, mostly but not exclusively a right angle, into the knee orthosis 51. By using at least one angle sensor 55 in the hinges of the connection element 52, and alternatively or cumulatively a force sensor 56 between connection element 52 and knee orthosis 51, an incorrect position of the hinge points after verticalization, or some other kind of slipping of the patient 90, can be detected, such that the process of automated adjustment is triggered and carried out as described above. This has the advantage, on the one hand, of automatic readjustment in the event of deviation from "ideal" angles and forces. Ideal angles could be defined, for example, such that a force N is always introduced perpendicularly with respect to the mattress 20, or tangentially with respect to the circular motion (or the trajectories T) which the knee 93 describes about the hip rotation point. The definition of "ideal" is to be defined by therapists and may be different from patient 90 to patient 90. The present invention thus allows the therapist to later choose how the forces N are introduced, depending on what the patient 90 needs, and this would not have to be set from the outset and could instead be modified over time, such that the rehabilitation mechanism 30 can be still better adapted individually to each patient 90.

Figure 11A:
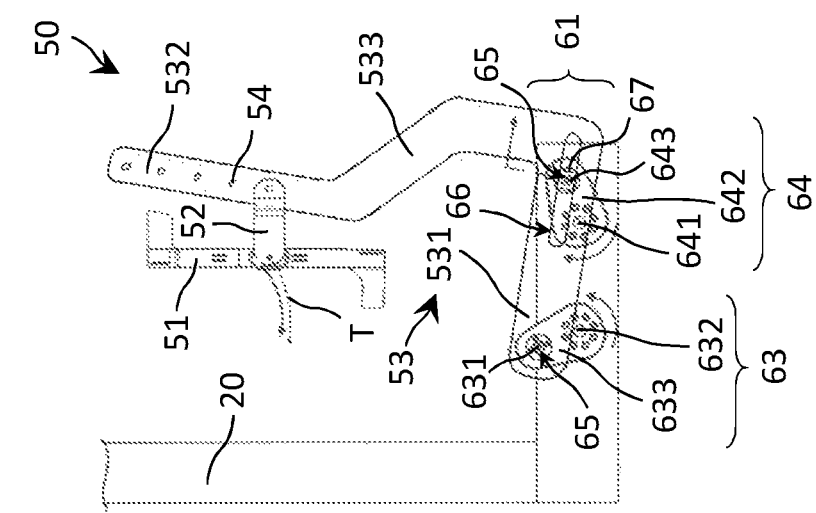
Figure 11B:
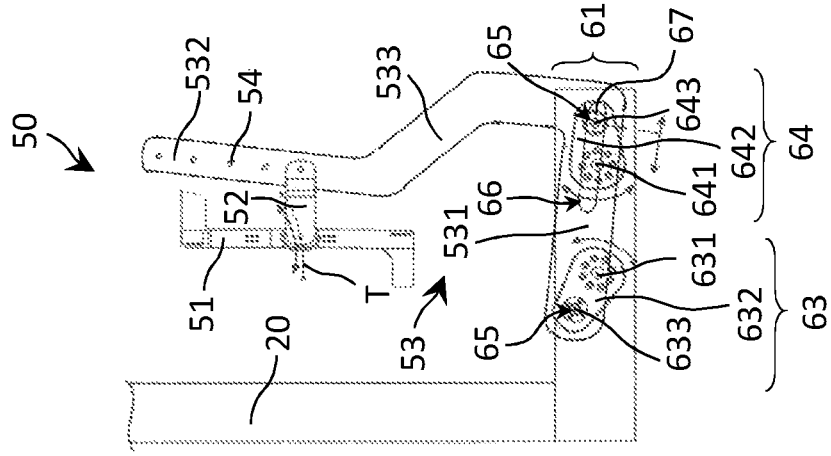
Figure 11C:
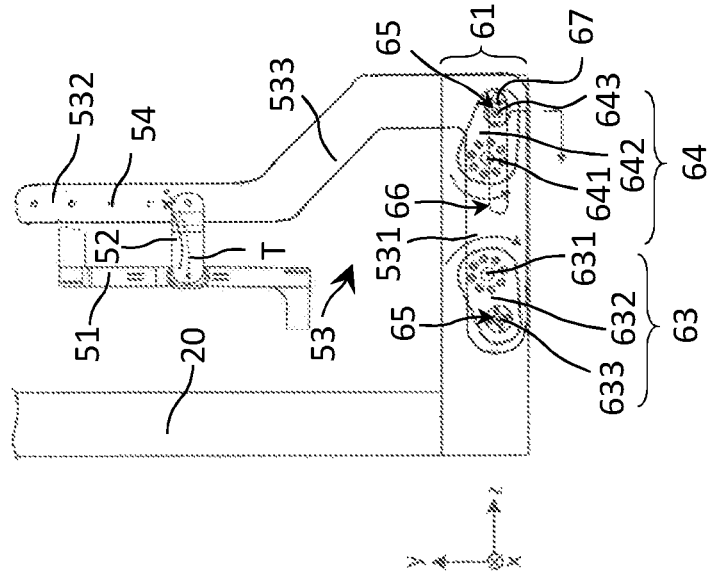

FIGS. 9a to 9c and FIGS. 11a to 11c show the trajectories (T) generated by the rehabilitation mechanism 30 via the knee orthosis 51, for bending or extending the legs 92 of a patient 90 with long legs 92 (FIGS. 9*a* to 9*c*) or with short legs 92 (FIGS. 11*a* to 11*c*).

As can be seen from FIGS. 9*a* to 9*c*, the connection element 52 in receiving point 54 on the extension arm 53 has a greater distance to the distal end or portion 531 of the extension arm 53 than in a patient 90 with a short leg length. This case is shown in FIGS. 11*a* to 11*c*, from which it can be seen that the connection element 52 in receiving point 54 on the extension arm 53 has a shortest distance to the distal end or portion 531 of the extension arm 53. In both cases, a stepping movement and/or a movement simulating the climbing of stairs can be generated for each patient 90, regardless of whether the patient has long or short legs 92.

FIGS. 9*a* and 11*a* show the initial state in which the connection element 52 and thus the knee orthosis 51 are located at the lowest point of the z axis and in which the leg 92 of the patient 90 is extended.

Through a combination of defined rotations of the eccentrics 63, 64, it is possible to travel the trajectories (T) shown by way of example in FIGS. 9*b* and 11*b*, which trajectories (T) correspond approximately to a rotation of the knee joint 93 about the hip joint of the patient 90. For a movement of the connection element 52 in a positive y and z direction, the first eccentric 63 rotates in a positive direction and the second eccentric 64 in a negative direction about the x axis. The linear guide in the sliding bearing 66 executes a movement in the y-z plane in the direction of the rotation point of the first eccentric 63, shown in FIGS. 9*a* and 11*a*.

For the movement in the negative y and z direction, shown in FIGS. 9*c* and 11*c*, the rotations of the eccentrics 63, 64 and the translational movement of the linear guide in the sliding bearing 66 are the opposite way round. FIGS. 9*c* and 11*c* moreover show the orientation of the eccentrics 63, 64 upon maximum deflection of the connection element 52 in the z direction and thus the position of maximum flexion of a leg 92 of the patient 90.

Between the therapy sessions, the knee module 50 and optionally also a foot module 40 can be removed from the patient 90 by the therapist and stowed away on the bed 10 or alternatively in the hospital room in such a way that, on the one hand, sufficient clearance is provided for movements of the patient 90 between the therapy sessions and, on the other hand, it is possible for the therapist to quickly reapply the components to the patient 90 and to the bed 10 or support plate 32. For this purpose, by way of the linear mechanism used for the adaptation to the leg width, it is possible for the foot module 40 to be shifted in the x direction to the outer edge of the mattress 20 and locked. The extension arms 53 can be detached from the eccentrics 63, 64, by release of the pin connections 633 and 634 secured for example by means of butterfly nuts 57, and folded aside. The knee orthosis 51 with connection element can be secured to the back of the foot plate 32 (cf. FIG. 2).

The present invention makes available a rehabilitation mechanism 30 which is improved over the prior art and which can be integrated without difficulty in all known clinical procedures, specifically for patients 90 who have become bedridden particularly on account of orthopedic, intensive care and/or neurological limitations on activity. Without having to transfer these patients 90 between beds, the present invention permits planned automated rehabilitation of at least the joints, muscles and tendons of the legs 92 of bedridden patients 90. On account of its modular construction, the rehabilitation mechanism 30 can be quickly removed and is not a hindrance in an emergency or in everyday clinical activity. The ability to load the feet 94 with the full or partial body weight of the patient 90 further trains the musculature and the skeleton and prevents degeneration of the musculo-skeletal system. A possibility of adopting a vertical position also trains the cardiovascular system.

This is equally important for orthopedic patients and likewise for intensive care patients and neurological patients 90. In addition to commercially available or specially made care beds or sickbeds 10, a rehabilitation mechanism 30 according to the invention can also be easily attached to and removed from commercially available or specially made hospital beds or intensive care beds 10, independently of whether the bedridden patient 90 in the respective bed 10 can be brought fully or partially to a vertical position, wherein the rehabilitation mechanism 30 supports a rhythmic loading and unloading of the soles 95 of the feet of bedridden patients 90 in any position adopted by the bedridden patient 10 between a horizontal and a vertical position.

With the present invention, it is in particular possible for the first time to carry out a method for actuating a rehabilitation mechanism 30, in which method the angle ($\varphi$) adopted by the connection element 52 to the knee orthosis 51 and/or to the extension arm 53 is monitored by means of at least one angle sensor 55;

and/or the force (N) introduced into the knee orthosis 51 via the extension arm 53 and the connection element 52 is monitored by means of a force sensor 56, wherein, if a variably predefined desired angle threshold ($\varphi$_desired) is exceeded or undershot and/or a variably predefined desired force threshold is exceeded or undershot, the control module 60 actuates the mechanical device 61 in such a way that the actual angle ($\varphi$_actual) and/or the actual force (N) are/is returned, by adjustment of the eccentrics 63 and 64 or of the eccentric disks 632, 642 thereof, to the desired angle threshold ($\varphi$_desired) and/or the desired force threshold below the exceeded thresholds or above the undershot thresholds.

FIG. 12 shows, in an enlarged view of the extension arm 53 from FIG. 8*c* for example, how the angle phi ($\varphi$) adopted by the connection element 52 to the knee orthosis 51 and/or to the extension arm 53 can be monitored by means of at least one angle sensor 55. It also shows the angles alpha ($\alpha$) and beta ($\beta$) which can each likewise be measured by means of an angle sensor (not shown) or represent a defined rotary angle position of the motor 62 driving the first eccentric 63 and/or the second eccentric 64.

The angle $\varphi$, monitored by at least one angle sensor 55, between the extension arm 53 and the connection element 52, which connects the extension arm 53 to the knee orthosis 51, should be able to adopt any therapeutically desired angle threshold ($\varphi$_desired). A desired angle threshold ($\varphi$_desired) can be indicated, for example, by 90° to the mattress 20. At this 90°, it is moreover preferable that the contact point at which the extension arm 53 is connected to the connection element 52 lies exactly above the rotation point of the knee orthosis 51.

FIG. 13 shows how, deviating from a desired angle setting ($\varphi$_desired), the knee joint 93 of a patient 90 can be shifted in the direction of the foot end of the bed 10. In this case I, the extension arm 53 has to be readjusted to a new, correct contact point, since otherwise the force (N), which is intended to be introduced to the knee joint 93 via the extension arm 53, the connection element 52 and the knee orthosis 51, cannot be introduced perpendicularly in particular.

In the case I shown in FIG. 13, the eccentrics 63 and/or 64 have to be adjusted, i.e. rotated toward each other as shown in FIG. 8a (specifically with the eccentric 63 belonging to the angle alpha being rotated counterclockwise, i.e. in the negative direction of rotation, and with the eccentric 64 belonging to the angle beta being rotated clockwise, i.e. in the positive direction of rotation) in order to shift the extension arm 53, as shown by means of an arrow in FIG. 13, linearly in the direction of the foot end of the bed 10. This can be effected, for example, by a controller which measures the actual angle phi (φ_actual) and adjusts this to a variably predefined desired angle threshold (φ_desired) of, for example, preferably 90 degrees, for example by means of a PID (proportional-integral-derivative controller).

FIG. 14 shows how, deviating from a desired angle setting (φ_desired), the knee joint 93 of a patient 90 can be shifted in the direction of the head end of the bed 10. Also in this case II, the the extension arm 53 has to be readjusted to a new, correct contact point, since otherwise a force (N), which is again intended to be introduced to the knee joint 93 via the extension arm 53, the connection element 52 and the knee orthosis 51, cannot be introduced perpendicularly in particular.

In the case II shown in FIG. 14, the eccentrics 63 and/or 64 likewise have to be adjusted, i.e. rotated toward each other as shown in FIG. 8c (specifically with the eccentric 63 belonging to the angle alpha being rotated clockwise, i.e. in the positive direction of rotation, and with the eccentric 64 belonging to the angle beta being rotated counterclockwise, i.e. in the negative direction of rotation) in order to shift the extension arm 53, as shown by means of an arrow in FIG. 14, linearly in the direction of the head of the bed 10. This can be effected, for example, by a controller which measures the actual angle phi (φ_actual) and adjusts this to a variably predefined desired angle threshold (φ_desired) of, for example, preferably 90 degrees, in particular by means of a PID controller.

According to the invention, the above-described adjustment of the eccentric disks 632, 642 can preferably be effected sequentially (i.e. independently of rehabilitation movements carried out as planned) or simultaneously with respect to rehabilitation movements carried out as planned.

FIG. 15 shows a schematic diagram of a control circuit for generating a planned rehabilitation movement by means of a rehabilitation mechanism 30, also designated as "robot" in FIG. 15. Accordingly, in a first step, the eccentric angles alpha(t) and beta(t) are fixed as a temporal sequence of desired angle combination pairs $$\begin{bmatrix} alpha(t) \\ beta(t) \end{bmatrix}.$$

The relationship between the change of the angles alpha and beta and the resulting movement of the extension arm 53 is shown and described in FIGS. 9a to 9c. By suitable actuation, the knee joint 93 of a patient 90 is advantageously moved such that the knee joint 93 moves on a circular trajectory T about the hip joint.

By comparing the actual angle (φ_actual) with the desired angle (φ_desired), an alpha/beta error can be calculated. This can then be corrected by a controller, e.g. a PID controller.

Finally, FIG. 16 shows a schematic diagram of a control circuit, expanded in relation to FIG. 15, for generating an adjustment of the eccentrics 63 and/or 64 of a rehabilitation mechanism 30, also designated as "robot" in FIG. 16, which adjustment takes place either sequentially or simultaneously with respect to planned rehabilitation movements.

If a planned rehabilitation movement is now carried out, it can happen that the patient 90 slips on account of the acting force N and/or on account of gravity. For example, this can also happen in particular when the bed 10 is moved to a vertical position and the forces of gravity push the patient 90 downward.

With the control circuit shown in FIG. 16, the adjustment of the eccentrics 63 and/or 64, i.e. the eccentric movement alpha and beta, can be effected simultaneously with respect to the planned rehabilitation movement. It is additionally possible in particular to insert a correction term which performs an adjustment in particular of the position of the proximal portion 532 of the extension arm 53, such that the actual angle phi (φ_actual) at each time follows its desired value $phi_{desired}$ (φ_desired). Described mathematically, this means a change of the phase lag between the eccentric rotation commands alpha(t) and beta(t) within the control system.

Thus, planned rehabilitation movements and adaptations of the position of the one or more contact points can be carried out simultaneously.

As an alternative to this, it is of course also possible to operate sequentially, in which case the planned rehabilitation movement is initially carried out for a defined time and then a renewed adjustment is carried out.

The present invention moreover has the advantage that a therapist can predefine which $phi_{desired}$ value the control module 60 corrects.

One possibility would be to keep phi (φ_desired) always at 90 degrees.

A further possibility would be to calculate the position of the extension arm 53 via the angles alpha and beta and thereby always determine the angle $phi_{desired}$ (φ_desired) according to alpha and beta, such that the connection element 52 between extension arm 53 and orthosis 51 is always perpendicular to the mattress 20.

A third possibility would be to control the angle φ_desired such that the connection element 52 between extension arm 53 and knee orthosis 51 is always tangential to the circular path, i.e. the circular trajectory T about the hip joint, which the knee joint 93 describes about the hip rotation point. In this way, φ_desired would be time-dependent on the predefined angle combination pairs $$\begin{bmatrix} alpha(t) \\ beta(t) \end{bmatrix}$$

of the eccentrics 63 and 64 and would be designated as φ_desired(t).

Finally, in a preferred embodiment, a therapist can advantageously make these decisions on an operating part of the control module 60.

LIST OF REFERENCE SIGNS 10 bed, in particular a care bed, sickbed, hospital bed or intensive care bed
11 bed frame
12 longitudinal sides
13 transverse sides
14 longitudinal barrier
15 transverse barrier 16 castors
20 mattress
21 mattress frame
30 rehabilitation mechanism
32 support plate, for rehabilitation mechanism 30, fastenable to the bed frame 11 or mattress frame 21
40 foot module
41 securing means
42 tread surface
43 fixing straps
50 knee module
51 knee orthosis
52 connection element
53 extension arm
531 distal portion of the extension arm 53
532 proximal portion of the extension arm 53
533 middle portion of the extension arm 53
54 receiving points
55 angle sensor
56 force sensor
57 butterfly nut
60 control module
61 mechanical device
62 electric motor
63 first eccentric
631 eccentric shaft of the first eccentric 63
632 eccentric disk of the first eccentric 63
633 control pin of the first eccentric 63
64 second eccentric
641 eccentric shaft of the second eccentric 64
642 eccentric disk of the second eccentric 64
643 control pin of the second eccentric 64
65 radial bearing
66 sliding bearing
67 slide block
70 adjustment mechanism
80 stabilizing mechanism
90 patient
91 chest—heart/lungs
92 leg
93 knee joint
94 foot
95 sole
N force
T trajectories

The invention claimed is:

1. A rehabilitation mechanism for a bed having longitudinal sides in a y-direction and transverse sides in an x-direction for a planned, automated rehabilitation of joints, muscles and tendons of the legs of a bedridden patient, the rehabilitation mechanism comprising:
a knee module to be operatively connected to a knee joint of the bedridden patient; and
a control module for controlling planned rehabilitation movements at least of the joints, muscles and tendons of a leg of the bedridden patient by way of said knee module;
said knee module being a module to be arranged in a z-direction above the patient and a mattress and to be supported directly or indirectly on a bed frame or a mattress frame, and said knee module including:
a knee orthosis configured to receive a knee joint of the bedridden patient;
a connection element connected to said knee orthosis;
an extension arm to which said connection element is secured; and
a mechanical device to be actuated by way of said control module and configured to introduce, by way of said extension arm and said connection element, a defined force into said knee orthosis in such a way that the joints, muscles and tendons of the leg perform planned rehabilitation movements via the bedridden patient's knee joint that is received in said knee orthosis;
said mechanical device including a first eccentric formed by a first eccentric disk mounted on an eccentric shaft and having a center point lying outside a shaft axis of said first eccentric shaft;
said mechanical device including a second eccentric formed by a second eccentric disk mounted on a second eccentric shaft and having a center point lying outside a shaft axis of said second eccentric shaft; and
said extension arm having a distal portion operatively connected to a control pin of said first eccentric disk via a radial bearing and operatively connected to a control pin of said second eccentric disk via a sliding bearing.

2. The rehabilitation mechanism according to claim 1, which comprises an electric motor disposed to drive said eccentric shafts.

3. The rehabilitation mechanism according to claim 1, wherein said sliding bearing is a slide block connected rotatably to the control pin of said second eccentric.

4. The rehabilitation mechanism according to claim 1, further comprising one or both of:
at least one angle sensor configured to monitor an angle adopted by said connection element to said knee orthosis and/or to said extension arm; and/or
a force sensor configured to monitor the force introduced into said knee orthosis via said extension arm and said connection element.

5. The rehabilitation mechanism according to claim 1, wherein said extension arm has a plurality of receiving points for mounting the connection element in an articulated manner, said plurality of receiving points being spaced apart from one another.

6. The rehabilitation mechanism according to claim 5, wherein said plurality of receiving points are spaced apart from one another at regular intervals.

7. The rehabilitation mechanism according to claim 1, further comprising a foot module which can be operatively connected to the feet or the soles of the bedridden patient.

8. The rehabilitation mechanism according to claim 7, wherein said foot module is configured to apply a torque to an ankle joint of the patient during a rehabilitation movement of the patient.

9. A bed for a bedridden patient, comprising the rehabilitation mechanism according to claim 1.

10. A method for actuating the rehabilitation mechanism according to claim 1, the method comprising:
monitoring with at least one angle sensor an angle adopted by the connection element relative to the knee orthosis and/or relative to the extension arm; and/or
monitoring of a force sensor a force introduced into the knee orthosis via the extension arm and the connection element;
if a variably predefined desired angle threshold is exceeded or undershot and/or a variably predefined desired force threshold is exceeded or undershot, actuating the mechanical device with the control module such that an actual angle and/or an actual force is returned, by adjustment of the first and second eccentric disks, to the desired angle threshold and/or the desired force threshold below the respectively exceeded thresholds or above the respectively undershot thresholds.

11. The method according to claim 10, which comprises effecting the adjustment of the eccentric disks independently from planned rehabilitation movements that are performed or simultaneously with respect to planned rehabilitation movements that are performed.

* * * * *